United States Patent [19]
Caetano-Anolles et al.

[11] Patent Number: 6,074,818
[45] Date of Patent: *Jun. 13, 2000

[54] FINGERPRINTING OF NUCLEIC ACIDS, PRODUCTS AND METHODS

[75] Inventors: Gustavo Caetano-Anolles, Knoxville, Tenn.; Brant J. Bassam, The University of Queensland, Australia; Peter M. Gresshoff, Knoxville, Tenn.

[73] Assignee: The University of Tennessee Research Corporation, Knoxville, Tenn.

[*] Notice: This patent is subject to a terminal disclaimer.

[21] Appl. No.: 08/139,459

[22] Filed: Oct. 20, 1993

Related U.S. Application Data

[63] Continuation-in-part of application No. 08/006,380, Jan. 19, 1993, Pat. No. 5,413,909, and a continuation-in-part of application No. 07/676,869, Mar. 28, 1991, abandoned, said application No. 08/006,380, is a continuation of application No. 07/573,627, Aug. 24, 1990, abandoned.

[51] Int. Cl.[7] .............................. C12Q 1/68; C07H 21/00

[52] U.S. Cl. ........................... 435/6; 435/91.1; 435/91.2; 435/810; 436/501; 536/23.1; 536/24.1; 536/24.3; 536/24.31; 536/24.32; 536/24.33; 935/77; 935/78; 935/88

[58] Field of Search ............................. 435/6, 91.1, 91.2, 435/810; 436/501; 536/22.1, 23.1, 24.1, 24.3–24.33; 935/77, 78, 88

[56] References Cited

U.S. PATENT DOCUMENTS

| | | | |
|---|---|---|---|
| 4,434,234 | 2/1984 | Adams et al. | 436/86 |
| 4,468,466 | 8/1984 | Morrissey | 436/86 |
| 4,555,490 | 11/1985 | Merrill | 436/86 |
| 4,575,452 | 3/1986 | Lee et al. | 422/61 |
| 4,582,808 | 4/1986 | Oudana et al. | 436/86 |
| 4,683,195 | 7/1987 | Mullies et al. | 435/6 |
| 4,683,202 | 7/1987 | Mullies et al. | 435/91.2 |
| 4,703,016 | 10/1987 | Merrill | 436/86 |
| 4,965,188 | 10/1990 | Mullis et al. | 435/6 |
| 5,043,272 | 8/1991 | Hartley | 435/5 |
| 5,102,785 | 4/1992 | Livak et al. | 435/6 |
| 5,126,239 | 6/1992 | Livak et al. | 435/6 |
| 5,437,975 | 8/1995 | McClelland et al. | 435/6 |
| 5,487,985 | 1/1996 | McClelland et al. | 435/91.2 |

FOREIGN PATENT DOCUMENTS

| | | |
|---|---|---|
| 0427074 | 5/1991 | European Pat. Off. . |
| 0466520 | 1/1992 | European Pat. Off. . |
| 0531027 | 3/1993 | European Pat. Off. . |
| 0534858 | 3/1993 | European Pat. Off. . |
| WO9114001 | 9/1991 | WIPO . |
| WO9203576 | 3/1992 | WIPO . |
| WO9207095 | 4/1992 | WIPO . |

OTHER PUBLICATIONS

Caetano–Anollés, et al., "Enhanced Detection of Polymorphic DNa by Multiple Arbitrary Amplicon Profiling of Endonuclease–Digested DNA: Identification of Markers Tightly Linked to the Supernodulation Locus in Soybean," *Mol. Gen. Genet.*, 241:57–64 (1993).

Caetano–Anollés, et al., "Primer–template Interactions During DNA Amplification Fingerprinting with Single Arbitrary Oligonucleotides," *Mol. Gen. Genet.*, 235:157–165 (1992).

Kernodle, et al., "Concentration of Primer and Template Quantitavely Affects Products in Random–Amplified Polymorphic DNA PCR", *BioTechniques*, vol. 14, No. 3, pp. 362–363 (1993).

Caetano–Anollés, et al., "DNA Amplification Fingerprinting Using Arbitrary Mini–hairpin Oligonucelotide Primers", *Bio/technology*, vol. 12, pp. 619–623 (1994).

Kleppe, K. et al., "Studies of Polynucleotides XCVI. Repair Replication of Short Synthetic DNA's as catalyzed by DNA Polymerases", *J. Mol. Biol.*, 56:341–361 (1971).

(List continued on next page.)

*Primary Examiner*—Ardin H. Marschel
*Attorney, Agent, or Firm*—Weiser & Associates, P.C.

[57] ABSTRACT

Improvements to nucleic acid fingerprinting are disclosed. The method generates profiles of increased fidelity characteristic of the nucleic acids analyzed. Novel primers and other means are taught. Useful products are disclosed.

83 Claims, 8 Drawing Sheets

OTHER PUBLICATIONS

Hirao, et al., "Extraordinary Stable Structure of Short Single-Stranded DNA Fragments Containing a Specific Base Sequence: d(GCGAAGC)," *Nucleic Acids Research,* vol. 17, No. 6, 2223–2231 (1989).

Hirao, et al., "Extraordinary table mini–hairpins: electrophoretical and Thermal Properties of the Various Sequence Variants of d(GCGAAGC) and Their Effect on DNA Sequencing," *Nucleic Acids Research,* vol. 20, No. 15, 3891–3896 (1992).

P.H. Dear and P.R. Cook, *Nucleic Acids Research,* 17:6795–6807 (1989).

Engelke, et al., *Proc. Natl. Acad. Sci. USA,* 85:544–548 (1988).

White, et al., *Sci. Am.,* 358:40–48 (1988).

Wong, et al., *Nature,* 330:384–386 (1987).

"Molecular Biology of Plants—Laboratory Course Manual", pp. 36–37 (1984).

New Riverdale University Dictionary (The Riverside Publ. Co., Boston MA 1984) p. 973.

Botstein, et al., *Am. J. Hum. Genet.,* 32:314–331 (1980).

Proudfoot, et al., *Science,* 209:1329–1336 (1980).

M.G. Murray, et al., *Nucleic Acids Research,* vol. 8, 19:4321–4325 (1980).

Jeffreys, *Cell,* 18:1–18 (1979).

Mullis, Kary B., "The Unusual Origin of the Polymerase Chain Reaction", *Scientific American,* pp. 56–65, Apr., 1990.

Van Brunt, Jennifer, "Amplifying Genes: PCR and its Alternatives", *Bio/Technology,* vol. 8, pp. 291–294, Apr., 1990.

Knight, Pamela, "Biosleuthing with DNA Identification", *Bio/Technology,* vol. 6, pp. 505–508, Jun., 1990.

Boulikas and Hancock, *Journal of Biochemical and Biophysical Methods,* 5:219–228 (1981).

Somerville and Wang, *Biochemical and Biophysical Research Communications,* 1:53–58 (1981).

Poehling and Neuhoff, *Electrophoresis,* 2:141–147 (1981).

Beidler, Hillard and Rill, *Analytical Biochemistry,* 126:374:380 (1982).

Guillemette and Lewis, *Electrophoresis,* 4:92–94 (1983).

Iglio, *Analytical Biochemistry,* 134:184–188 (1983).

Kolodny, *Analytical Biochemistry,* 138:66–67 (1984).

Gottlieb and Chavko, *Analytical Biochemistry,* 165: 33–37 (1987).

Rabilloud, *Electrophoresis,* 11:785–794 (1990).

Allen, et al., *Biotechniques,* 7:736–744 (1989).

Blum, et al., *Electrophoresis,* 8:93–99 (1987).

Bassam, et al., *Analytical Biochemistry,* 196:80–83 (1991).

Lomholt, et al., *Analytical Biochemistry,* 164:146–149 (1987).

Kalisch et al. (1986) Gene, 44, pp 263–270.

6,074,818

```
                         SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (xi) SEQUENCE DESCRIPTION: SEQ ID NO:1:

GCGAAGCCCG AGCTG                                                      15

(2) INFORMATION FOR SEQ ID NO:2:

(i) SEQUENCE CHARACTERISTICS:
         (A) LENGTH: 13 base pairs
         (B) TYPE: nucleic acid
         (C) STRANDEDNESS: single
         (D) TOPOLOGY: linear (xi) SEQUENCE DESCRIPTION: SEQ ID NO:2:

GCGAAGCGAG CTG                                                        13

(2) INFORMATION FOR SEQ ID NO:3:

(i) SEQUENCE CHARACTERISTICS:
         (A) LENGTH: 11 base pairs
         (B) TYPE: nucleic acid
         (C) STRANDEDNESS: single
         (D) TOPOLOGY: linear (xi) SEQUENCE DESCRIPTION: SEQ ID NO:3:

GCGAAGCGCT G                                                          11

(2) INFORMATION FOR SEQ ID NO:4:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (xi) SEQUENCE DESCRIPTION: SEQ ID NO:4:

GCGAAGCCTG                                                            10
```

(2) INFORMATION FOR SEQ ID NO:5:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:5:

GCGAAGCNCT G                                                         11

(2) INFORMATION FOR SEQ ID NO:6:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:6:

GCGAAGCNAG CTG                                                       13

(2) INFORMATION FOR SEQ ID NO:7:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:7:

GCGAAAGCGA GCTG                                                      14

(2) INFORMATION FOR SEQ ID NO:8:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:8:

GCGTTAGCGA GCTG                                                      14

(2) INFORMATION FOR SEQ ID NO:9:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:9:

GCGAAAGCGC TG                                                        12

(2) INFORMATION FOR SEQ ID NO:10:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:10:

NNCCGAGCTG                                                           10

(2) INFORMATION FOR SEQ ID NO:11:

```
    (i) SEQUENCE CHARACTERISTICS:
        (A) LENGTH: 10 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 1
        (D) OTHER INFORMATION: /mod_base= i (ix) FEATURE:
        (A) NAME/KEY: modified_base
        (B) LOCATION: 2
        (D) OTHER INFORMATION: /mod_base= i (xi) SEQUENCE DESCRIPTION: SEQ ID NO:11:

NNCCGAGCTG                                                              10

(2) INFORMATION FOR SEQ ID NO:12:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:12:

CCGAGCTGNN                                                              10

(2) INFORMATION FOR SEQ ID NO:13:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 9
        (D) OTHER INFORMATION: /mod_base= i (ix) FEATURE:
        (A) NAME/KEY: modified_base
        (B) LOCATION: 10
        (D) OTHER INFORMATION: /mod_base= i (xi) SEQUENCE DESCRIPTION: SEQ ID NO:13:

CCGAGCTGNN                                                              10
```

FINGERPRINTING OF NUCLEIC ACIDS, PRODUCTS AND METHODS

RELATED PATENT APPLICATIONS

This patent application is a continuation-in-part of patent application Ser. No. 08/006,380, now U.S. Pat. No. 5,413,909, filed Jan. 19, 1993, entitled "Methods for Profiling Nucleic Acids of Unknown Sequence Using Arbitrary Oligonucleotide Primers", which is in turn a continuation application of application Ser. No. 07/573,627, filed Aug. 24, 1990, now abandoned, inventors, Gustavo Caetano-Anolles, Brant Bassam and Peter Gresshoff.

This patent application is also a continuation-in-part of Ser. No. 07/676,869, "the second parent" application, filed Mar. 28, 1991, now abandoned, entitled "DNA Silver Staining", inventors, Gustavo Caetano-Anolles, Brant Bassam and Peter Gresshoff, which is also incorporated herein by reference.

That application "the first parent" application is incorporated herein by reference. The method has been nick-named "DAF". It provides the highest resolution of fingerprint product known to date. Any sequence of nucleotides may be used as a DAF primer so long as the same sequence is used when comparing different DNA samples. Although a particular nucleotide sequence may be used according to the method of the invention, it is not necessary to use a particular nucleotide sequence for the primers of the present invention. It is necessary however, to use the same primer when comparing different samples for polymorphisms.

FIELD OF THE INVENTION

The invention relates to nucleic acid "fingerprinting of nucleic acids".

BACKGROUND OF THE INVENTION

A novel method for DNA fingerprinting that uses at least one oligonucleotide to prime arbitrary segments of a DNA template to produce a characteristic set of amplified fragments is being shown to be of increasing value in the analysis of genetic relationships. Fingerprint complexity varies from very simple, and thus ideal for genome mapping, to highly complex and more suitable for fingerprinting. See *Bio/Technology*, Vol. 10: 937, September 1992 incorporated herein by reference and attached (Exhibit 1).

DNA amplification fingerprinting (DAF) is the enzymatic amplification of arbitrary stretches of DNA which is directed by short oligonucleotide primers of arbitrary sequence to generate complex but characteristic DNA fingerprints.

The restriction mechanism proposed by the inventors can be seen in Amplifying DNA with Arbitrary Oligonucleotide Primers, Review 1993, Cold Spring Harbor Laboratory Press which is incorporated herein by reference and attached hereto (Exhibit 2). Of particular interest is the description of the step by step amplification described at pages 2 and 3.

Terms and terminology used in conjunction with the invention are known in the art. For instance, "oligonucleotide", "primer", "restriction endonuclease" and "restriction enzymes", "DNA polymorphism", "Restriction fragment, length polymorphism", ("RFLP"), "random nucleic acid fragment", "DNA fingerprinting", or "DNA typing", "genotyping", "profiling", "DNA identification analysis", or "DNA polymorphism", "polymerase chain reaction" ("PCR"), "DNA amplification", "random amplified polymorphic DNA" ("RAPD"), "amplicons" and "DNA amplification fingerprinting" ("DAF") are discussed in the patent and other scientific literature, such as in the U.S. Pat. Nos. 4,683,202 (Mullis), 5,126,239 (Livak et al.), PCT Publication No. WO 92/03567 Caetano-Anolles et al., which are incorporated herein by reference. For "Genomes" ("complex and simpler", see Genes IV by Benjamin Lewin, Chapter 24 (1990), ranging from as little as $10^6$ for a mycoplasma to as much as $10^{11}$ bp for some plants and amphibians, which is incorporated herein by reference.

SUMMARY OF THE INVENTION

Figures 1A, 1B, 1C:
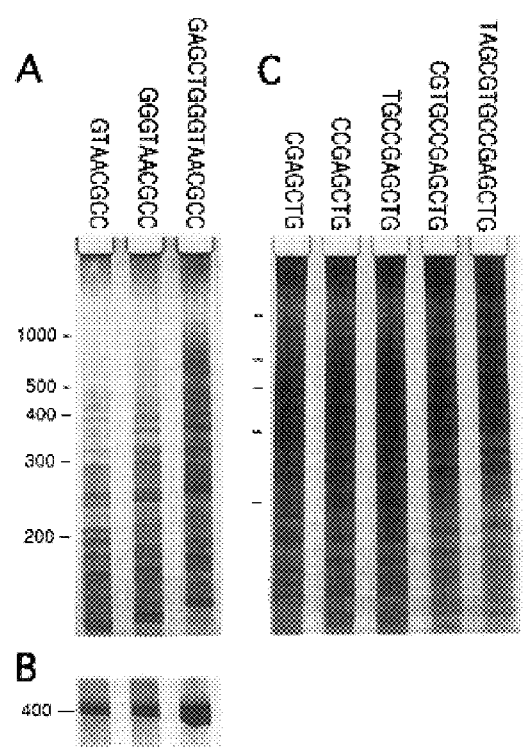
FIG. 1A shows photographs of gels of profiles obtained following reamplification with primers of varying lengths wherein EDNA sequences from *E. coli* were originally amplified using octamer primers GTAACGCC (1A) and CCGAGCTG (1C).
FIG. 1B shows gels obtained following reamplification with primers of various length of an isolated an purified product or original amplification using GTAACGCC.

The present invention provides novel improvements in methods and products in DNA amplification fingerprinting (DAF). Products of the invention provide improvements not only in DAF, but also in multiple arbitrary amplicon profiling (MAAP) techniques, like in random amplified polymorphic DNA (RAPD) analysis or modifications thereof.

The invention provides a method of reamplifying nucleic acid product(s) of DAF to synthesize nucleic acid sequences extended at the 5' end by functional regions.

Another embodiment of the invention provides novel oligonucleotide primers, particularly short primers, with a 3' end of a defined number of nucleotides and their use in DAF or in other MAAP techniques.

An important embodiment of the invention provides various techniques and means to decrease amplification from mismatched primers and to optimize product formation resultant from the functions of the 3' end of the primer.

In another embodiment, the invention provides novel arbitrary oligonucleotide primers which include at the 5' end, a hairpin structure or other equivalent structure and their use in DAF or in other MAAP techniques.

In another somewhat related embodiment, the invention provides novel arbitrary oligonucleotide primers which comprises purine or pyrimidine substituted polyamide (PNA, for polyamide nucleic acid) and their use in DAF or in other MAAP techniques.

The invention further provides multiple endonuclease digestion of selected template DNA followed by the treatment of the DNA digestion by DAF or other MAAP techniques.

The invention provides the use of improved highly thermostable DNA polymerases, truncated derivatives of *Thermo aquaticus* (AmpliTaq), which are especially well suited for use in DAF and other MAAP techniques.

In accordance with the invention, there are provided improved nucleic acid amplification parameters for DAF such as cycling conditions, e.g. temperature, amounts of primer relative to nucleic acid template, the concurrent use of multiple primers, and other aspects that will become apparent from the more detailed description of the invention.

The various methods and products of the invention provide remarkable increase in information content (i.e. number of bands and polymorphisms) of fingerprints generated with the selected primer(s).

In accordance with the invention it should be noted that the various improvements in methodology and new products herein disclosed can be used individually in conjunction with what is called the DAF method, in general, the MAAP methodologies, or in any combination thereof. For instance, the important feature of the invention as used hereinafter of using an arbitrary mini-hairpin oligonucleotide primer for nucleic acid amplification fingerprinting with only 3 terminal (3' end) single stranded nucleotides may be applied to any of the existing MAAP techniques like DAF or others which will be hereinafter described. The same observation applies to other embodiments disclosed herein.

DETAILED DESCRIPTION OF THE PREFERRED EMBODIMENTS OF THE INVENTION

A method of the invention comprises amplifying nucleic acid fragment(s) obtained from DAF with at least one arbitrary primer which has a common sequence with and which may be shorted, but preferably is longer than the primer used in the first amplification. For reamplification with the primer of selected length, a mixture of nucleic acid fragments or a single isolated nucleic acid fragment, preferably purified product obtained from a first amplification, may be used as the template.

Figure 3A:
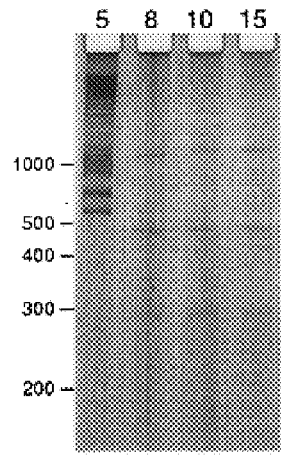
FIG. 3 shows photographs of gels of profiles produced following reamplification using amplification primers of 5, 8, 10, and 15, bases in length, and reamplification primers of 5 bases (3A) and 8 bases (3B) in length.
Figure 3B:
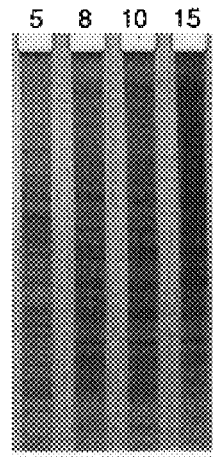

A method of reamplification is further described in *Mol. Gen. Genet.* 235:157–165 (1992) ("MGG 1992") which is incorporated herein by reference be made a part of this disclosure and attached hereto as Exhibit 3. In FIGS. 3A–C of MGG 1992 it will be seen that primers of different lengths sharing a common sequence are shown amplifying a single isolated and purified product or a mixture of products obtained from a first amplification with octamers.

DNA fragments that had previously been amplified with octamers were used as templates for subsequent amplification with longer and shorter related primers. Primers of varying lengths derived from a common sequence were used to reamplify products originally produced from *E. coli* DNA using the octamers GTAACGCC (FIGS. 1A and 1B of the specification and FIGS. 3A and 3B of MGG 1992) and CCGAGCTG (FIG. 1C of the specification and 3C of MGG 1992). Longer primers, which would produce 5' overhangs on primer-template duplexes during annealing with the original template sequences, amplified template DNA in all cases. In the amplification of complex template mixtures, almost identical patterns were produced with primers of different lengths, with tine expected mobility shift towards higher molecular weight.

Reamplification experiments using a shorter primer (a heptamer that would leave a single nucleotide overhang at the 3' terminus of the template, produced an amplification pattern in which some of the expected dominant products failed to amplify (FIG. 1C of the specification and FIG. 3C of MGG 1992). Similarly, longer primers (that produce primer-template duplexes having 5' overhangs) resulted in several amplification products disappearing. These results indicate that overhangs in both strands of primer-template duplexes (produced as a result of differences in primer length) condition the formation of many amplification products, despite perfect complementarity.

Figure 2A:
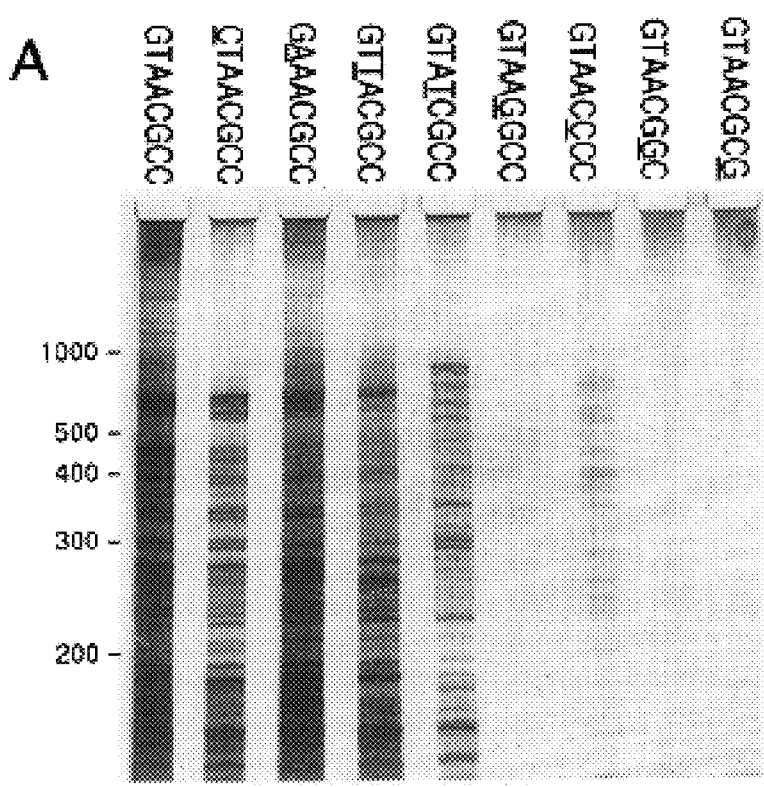
FIG. 2 shows photographs of gels of profiles obtained using various primers having identical lengths and different sequences.
Figure 2B:
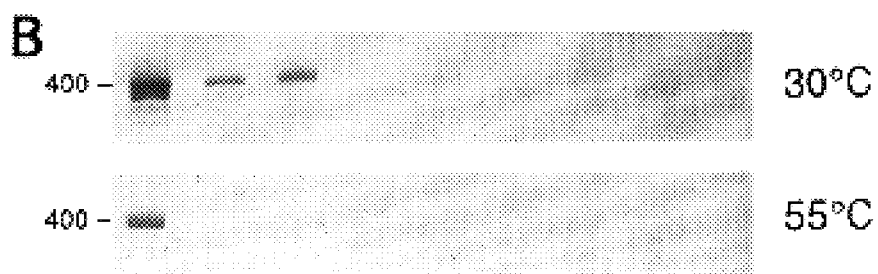

A set of primers with single base substitutions was used to reamplify DNA that had originally been amplified with the octamer GTAACGCC. (FIG. 2 of the specification and FIG. 5A of MGG 1992). Primers that would produce mismatches at the 5'-terminal region of the primer-template duplexes were able to amplify the majority of products.

Figures 5A, 5B:
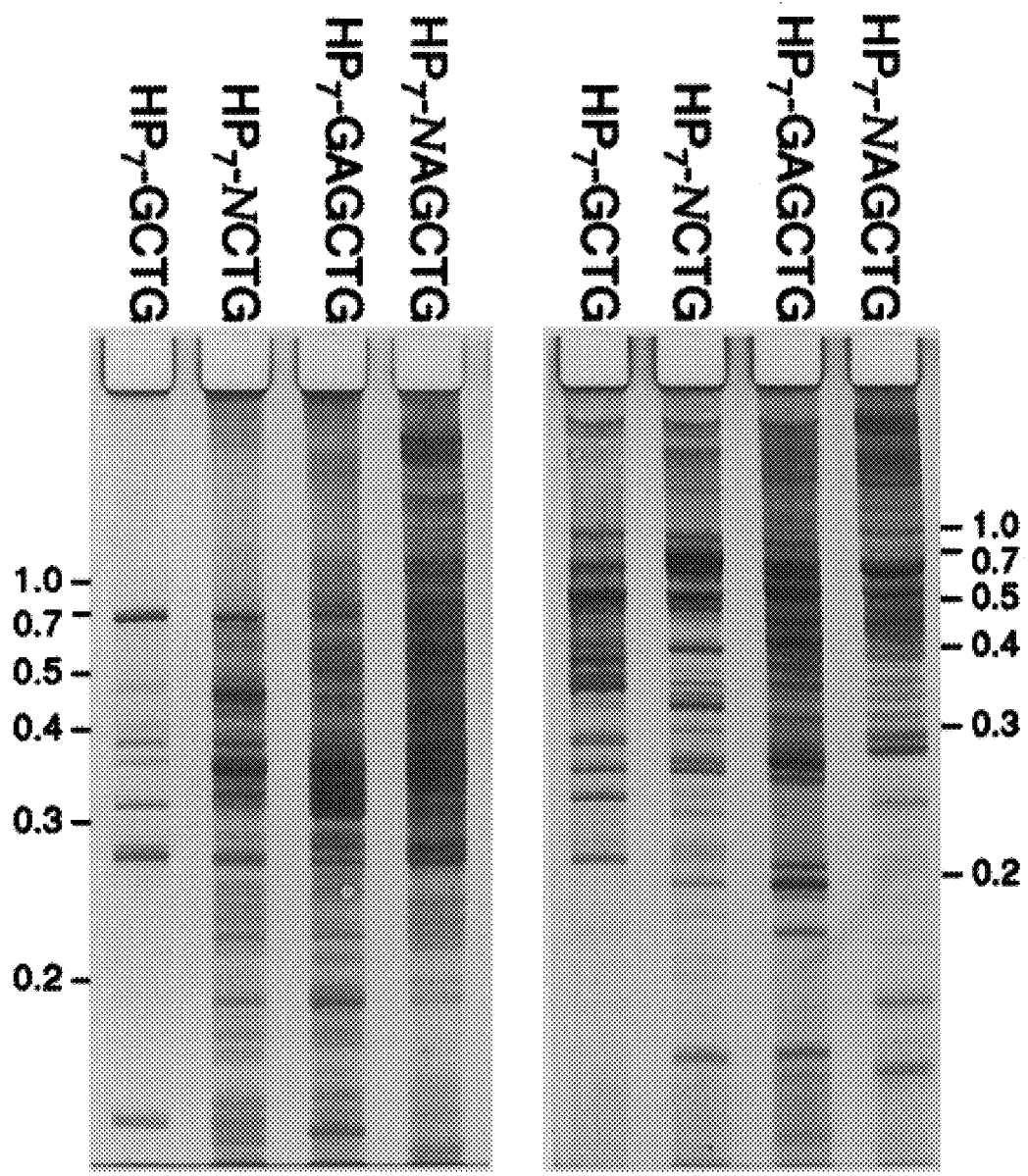
FIG. 5 shows photographs of gels of profiles obtained from DNA of soybean (A) and of *E. coli* (B), using typical hairpin primers with different hairpins.
Figure 6A:
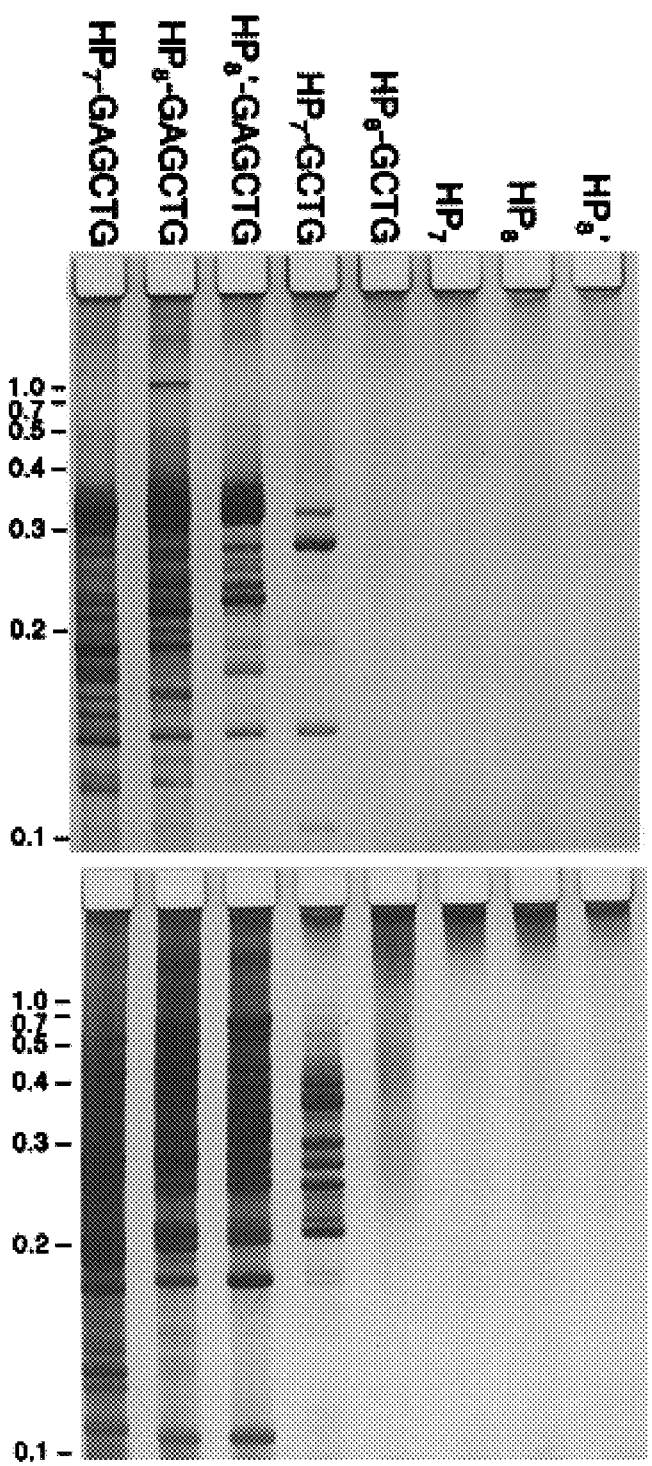
FIG. 6A shows photographs of gels of profiles obtained from DNA of soybean (gel A) and *E. coli* (gel B).
Figure 6B:
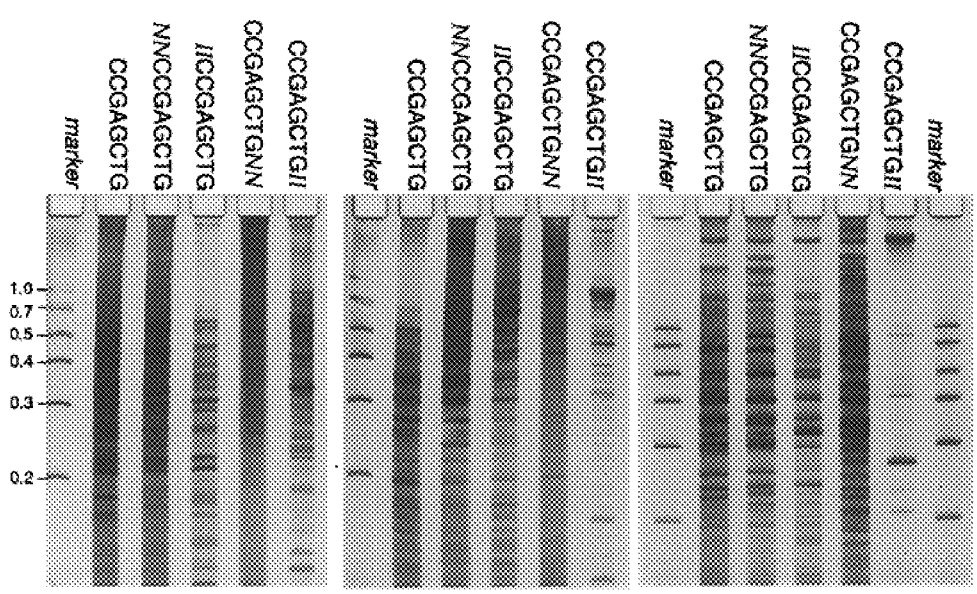
FIG. 6B shows photographs of gels obtained from DNA of fruit bat (gel A), soybean (gel B), and *E. coli* (gel C) in which the primers have certain bases substituted at the 3' end or 5' end, as illustrated by I and/or by N, N representing any one of the four bases.

FIGS. 5A, 5B, of MGG 1992 show the reamplification of all products of a single isolated and purified product obtained from using the shown octamer. Conversely, a pentamer and an octamer were used to reamplify the products originally generated by primers as shown in FIGS. 6A and 6B of MGG 1992.

A set of related oligonucleotides of decreasing lengths originating from the oligonucleotide sequence TAGCGT-GCCGAGCTG was used to reamplify DNA originally amplified with these same primers. The pentamer AGCTG, in FIGS. 3A of the specification and 5A of MGG 1992, or the octamer CCGAGCTG, in FIG. 3B of the specification and 5B of MGG 1992, were used to reamplify products originally produced from *E. coli* DNA using primers of increasing length: 5, AGCTG; 8, CCGAGCTG; 10, TGC-CGAGCTG; 15, TAGCGTGCCGAGCTG. When amplification was directed by a pentamer, only the template DNA with 5-base terminal symmetry was amplified. However, when an octamer was used to direct amplification, all templates were amplified.

The reamplification fragments comprise at their respective 5' end an additional sequence which causes a shift in the visualization bands, which provides additional information about the nucleic acids analyzed.

Of great practical interest are such reamplification products which comprise selective tailored extended 5' end sequences for selected uses, for instance as hybridization probes for diagnostic use in targeting a gene and other uses. The products should be distinguished from DNA fragments with ligated ends of desired sequences.

Primers longer than 8 nucleotides, like 12 and 15 nucleotides, which produce 5' overhang on primer-template duplexes during annealing with the original template sequence, amplified template DNA in all cases. Larger primers, e.g. 30 nucleotides in length may be considered depending on the use intended for the products. Preferably, it is primers of at least 8 nucleotides in length which are extended as described herein.

The invention provides a further important embodiment which relates to primers. The prior art generally teaches that the minimum useful primer length is an oligonucleotide of 9 bases (Williams et al. (1990), the RAPD method). The first parent application to the present application proposes at least 5 nucleotides for successful amplification and product visualization. It has now been discovered that in any length oligonucleotide primer it is the first 5 nucleotides from the 3' end which define what is called here the "core" region. Without these 5 nucleotides, no priming event is likely to take place. The next region comprising from nucleotide 6 to 8 hereby defined as the "optimizer" region, contributes to more efficient amplifications. It is the region which plays an important role in recognizing the priming target site. The following basic domain from 9 upward, for instance to 30, is considered a "5' extension tail" region. These additional nucleotides will alter the amplified spectrum only moderately. In accordance with the inventors' view, the primers thus can be considered as comprising starting from the 3' end, a core of 5 nucleotides followed by a domain "the optimizer" to a length of primers to a total of 7 or 8 nucleotides. For amplification of genomes of greater complexity like soybean and human, preferably the primer will contain 8 nucleotides and it will contain 7 nucleotides for simpler genomes, like for bacteria and fungi. Addition of nucleotides to the 7 or 8 nucleotide domain, respectively, does not increase the information content of DNA patterns significantly. Thus, in accordance with the invention, the core and the optimizer domains are the major determinants of the amplification reaction, conditioning the number and nature of amplification products produced. However, as taught hereinafter, it has been unexpectedly discovered in accordance with the invention that the core sequence can be reduced to 3 nucleotides.

These observations were based on studies where sets of related oligonucleotides where designed by removing nucleotides from the 5' end of an arbitrarily chosen sequence then used to direct amplification of several templates. Patterns generated by related primers of 5 to 8 nt in length were different in complexity and band distribution. Surprisingly, increasing primer length increased the number of amplification products. In contrast, primers of 8 and 10 nt in length produced virtually identical patterns, while patterns generated with longer primers were again divergent but showed some common bands. Base substitutions in the last two 5'-terminal nucleotides produced several variant amplification fragments, but the overall patterns remained very similar. This (as noted above) indicates that sequences beyond the 8 nt 3'-terminal region affect amplification only moderately.

We used related oligonucleotides differing in length or sequence, and templates engineered to have complementary or mismatched terminal sequences of varying length, to study primer-template interactions established during DAF. The short oligonucleotides used in these experiments approached their functional limits as primers for amplification. Our study defined several domains in the primer-template duplex, see FIG. 7. The first 8 nucleotides from the 3' terminus of the primer encompassed a region largely responsible for directing the amplification process. Single base changes in sequence within this domain altered the spectrum of amplification products significantly, especially toward the 3' terminus. Results show the importance of the 3'-terminal region of the primer in the DAF reaction and confirm observations for PCR.

Whereas successful amplification requires a primer of at least 5 nucleotides in length and annealing sites with perfect homology to the first 5 or 6 nucleotides from the 3' terminus, decreasing primer length within the 8-nucleotide domain results in an unpredicted decrease in the number of amplification products and in the production of highly variant fingerprint patterns. In theory, primers of increasing length derived from a common sequence should target subsets of sites recognized by shorter primers, and a common pattern should dominate all fingerprints. As this was not the case, results suggest that only a fraction of template-annealing sites amplify efficiently. Furthermore, certain amplicons are amplified preferentially by short primers due to competition for annealing sites between primer and terminal hairpin loop structures of the template. Primers 8 nucleotides or longer were better able to complete for annealing with hairpin loops.

Figure 7:
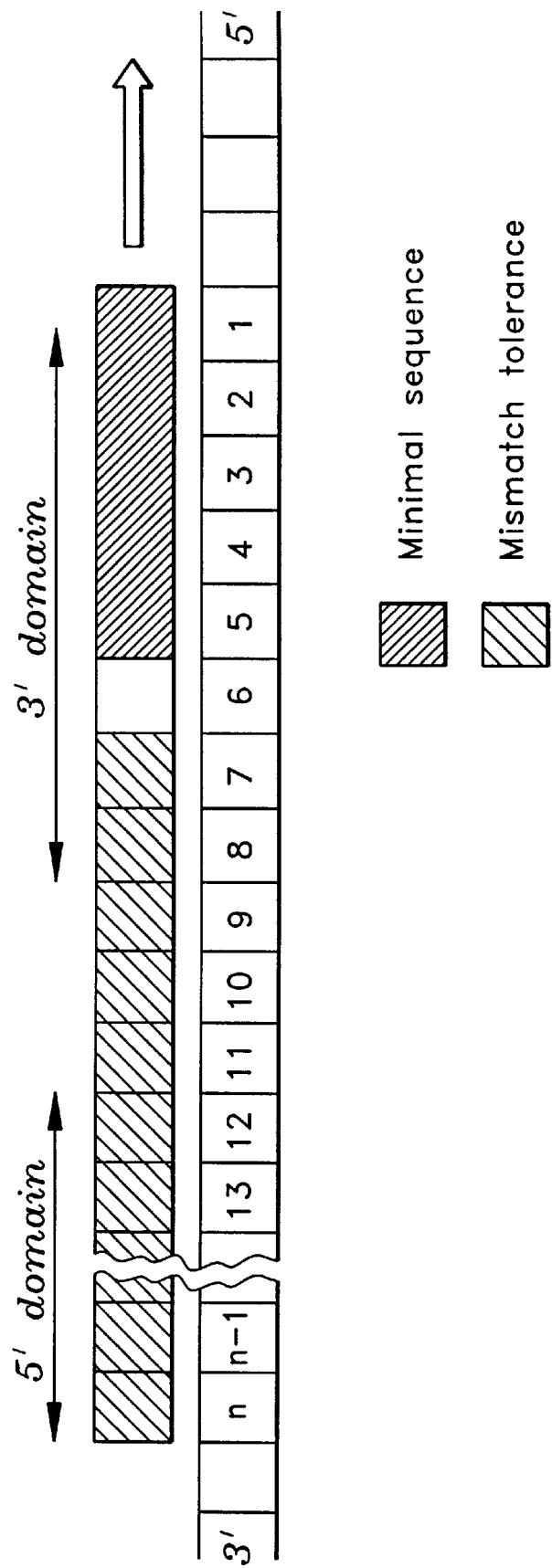
FIG. 7 shows the primer-template duplex domains established during amplification with arbitrary primers. The first 5 nucleotides at the 3' end of the primer, the core region as shown, are complementary to the template. Any one or more, up to all, of the nucleotides towards the 5' side of the core region, which is the optimizer and extension tail regions, may be non-complementary to the template.

Regions beyond the basic 8-nucleotide domain alter the amplified spectrum only moderately. In particular, the domain is demarcated by a 2- to 3-nucleotide region over which changes in primer length do not alter fingerprint pattern (FIG. 7). Increasing the primer length does not decrease the number of amplification products. This and the following lines of evidence suggest primer-template mismatching at the 5' end of the primer. First, amplification of genomes of high complexity like soybean and human with primers of >8 nucleotides in length and of bacteria and fungi with primers of >7 nucleotides in length produce many more products than expected. Similarly, primers comparable with those used in PCR produced AP-PCR and RAPD fingerprints from bacterial fungal, plant, and animals species, where no products were to be expected on theoretical grounds (unless the primer recognizes disperse repetitive sequences). Second primers of 8 and 10 nucleotides in length produced identical fingerprint patterns from an array of organisms ranging from bacteria to human. Third, cleavage of template DNA with up to five restriction endonucleases with 4 bp-recognition sequences prior to amplification did not decrease the number of amplification products. Destruction of bona fide amplicons by cleavage must then permit amplification of products resulting from at least single mismatch events at the primer 5' terminus. Fourth, octamers with single base substitutions at the 5' end were still able to amplify product with defined 8 nucleotide termini by prior amplification. Mismatches in the first 2–3 nucleotides from the 5' end allowed amplification of almost all products. Mismatches at positions more distant from the 5' terminus failed to initiate amplification. Fifth, cloning and sequencing of genomic regions that hybridized to several amplification fragments revealed mismatches at the 5' terminus.

Addition of nucleotides to the 8 nucleotide domain does not increase the information content of DNA patterns significantly. This observation suggests that longer primers such as those used in other studies may not be required. The 5' terminus of primers of a length comparable with those used in PCR, however, may condition fingerprint patterns significantly. This is expected because long 5'-terminal primer domains may contain regions of partial homology to the template, favoring some amplicons over others.

These and related studies suggest that longer primers such as those used by other known methods may not be required. Such methods are in effect using the first 5–8 nucleotides of the 3' end of the primer effective domain. For further description of these aspects of the invention, reference is made to Amplifying DNA with Arbitrary Oligonucleotide Primers, Gustavo Caetano-Anolles, cited above.

Although in the first parent case, the use of pentamers was taught, the full significance of the role of the various component domains of longer primers was not fully appreciated.

In connection with primers, it is noted that U.S. Pat. No. 5,126,239 to Livak et al. teaches that it is preferable that the primer contain sequences that do not form a "hairpin" configuration. In accordance with the present invention, it has been found most unexpectedly that what appeared heretofore to be close to the functional limit for priming DNA amplification (5 oligonucleotides) is reducible even further to 3 nucleotides. In accordance with the invention, these primers comprise at the 3' end, 3 nucleotides and a hairpin at the 5' end. These primers are called herein "hairpin or mini-hairpin primers". These arbitrary primers, unlike other primers used heretofore in fingerprinting unexpectedly need only a minimum of a combination of any three nucleotides at the 3' end to amplify arbitrary stretches of nucleic acids from a nucleic acid template.

Figures 4A, 4B, 4C, 4D:
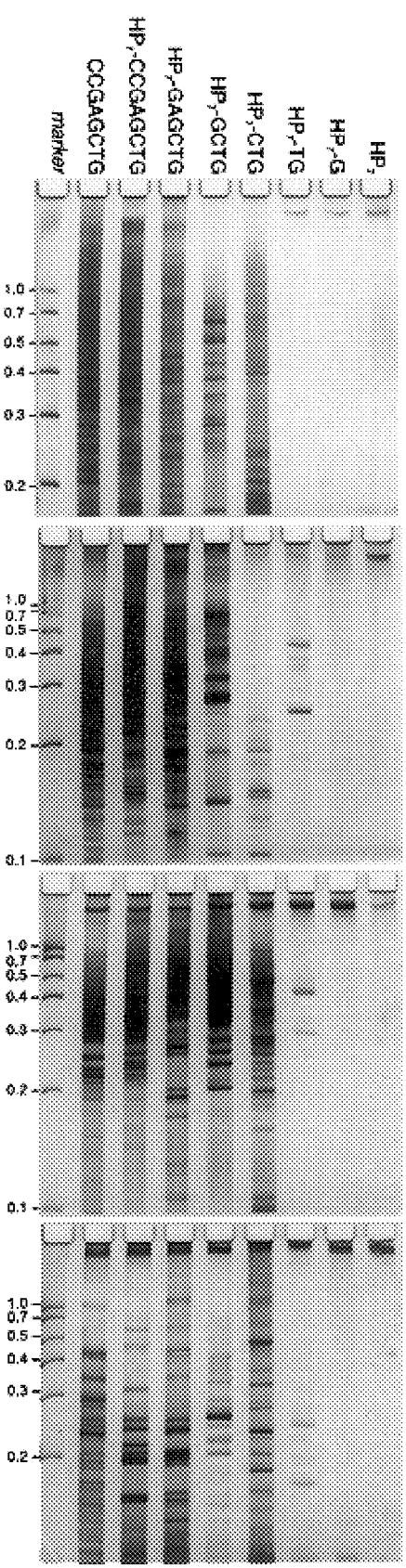
FIG. 4 shows photographs of gels of profiles obtained from DNA from indonesian fruit bat (A), soybean (B), *E. coli* (C), and bacteriophage lambda (D), using hairpin primers $HP_7$ and different primer sequences.

FIG. 4 shows the use of sequence related primers having at the 5' end a mini-hairpin (HP$_7$) of sequence GCGAGC for the amplification of DNA.

Panel A shows amplification of DNA from indonesian fruit bat (*Pteropus Hypomelanus*) soybean (*Glycine max* cv. Bragg) (Panel B) bacterium (*E. coli* strain Smith92) (Panel C), and bacteriophage (Lambda cI857ind1Sam7) (Panel D).

This and related work shows that a mini-hairpin primer with only a 3 base pair arbitrary domain (in the case, illustrated, CTG) produce reproducible fingerprints. It is to be noted that the hairpin sequence HP$_7$ per se is unable to produce any fingerprints, indicating that the most active annealing sequence is that of the 3' end.

It is not to be totally excluded that under other experimental conditions a primer with a domain with less than 3 base pairs could adequately produce reproducible fingerprints.

While it is not intended to be limited by this theory, it appears that amplification products initiated by a single primer share the particular characteristic of having a region of terminal hairpin symmetry at least as long as the primer itself. For efficient amplification of these products to occur, the primer should displace these hairpin loop complexes long enough for the DNA polymerase to anchor and stabilize the duplex by strand extension. The extent of hairpin loop interference will be variable for each fragment, allowing some fragments to be preferentially amplified. Studies in relation to this aspect of amplification by primers of increasing length suggests that when the primer is longer than the 8-nucleotide domain, it is better able to compete for annealing with hairpin loops. This may be the reason why conventional fingerprinting methodology teaches using primers greater than 8 nucleotides in length. See Williams et al. 1991. Unexpectedly, it has been discovered, however that it is only necessary for the arbitrary mini-hairpin oligonucleotide primers to have at the 3' end 3 nucleotides which basically determine amplification. It may be that the hairpin primers of the invention inhibit hairpin formation on the amplification products and make more priming sites accessible than heretofore available.

A most interesting consequence of this finding in accordance with the invention is that the invention now provides a close set of 64 different primers, which is the total of all combinations in a sequence of nucleotides containing any of the known 4 bases of DNA.

Accordingly, the invention provides a kit for amplification which comprises 64 different primers of 3 nucleotides of arbitrary sequence at its 3' end and a hairpin loop constituting the 5' end.

An illustrative mini-hairpin primer can be represented as follows:

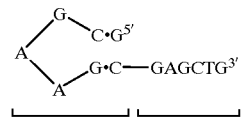

where the 3' region is constituted of 4 nucleotides GCTH3', and the hairpin is constituted of a stem of 2 nucleotides of complementary bases and a single stranded loop of 3 nucleotides. Another primer was constructed with the same hairpin and CTG at the 3' end. Other illustrative primers are HP$_7$-CTG, HP$_7$-GCTG, HP$_3$-GAGCTG, HP$_7$-CCGAGCTG. See FIG. 4 which shows the use of sequence related primers having at the 5' end a mini-hairpin HP$_7$ of sequence GCGAAGC for the amplification of DNA. Other primers synthesized included HP$_7$=GCGAAGC, HP$_8$=GCGAAAGC and HP$_8$=GCGTTAGC. FIG. 5 shows other mini-hairpins when amplifying soybean cv. Bragg or *E. coli* (isolated Smith 92), panel A and B, respectively. The mini-hairpins have the following sequence: HP$_8$-GCTG, HP$_7$-GCTG, HP$_8$-GAGCTG, HP$_8$-GAGCTG, HP$_7$-GAGCTG, HP$_7$-NCTG, HP$_7$-NAGCTG.

Many sequence variants for the hairpin loop of the 5' end of the primer form stable mini-hairpins in a similar manner as the HP$_7$. For instance, DNA fragment, d(GCGAAAGC) forms a stable hairpin structure consisting of a GAAA loop and only 2 GC pairs at the stem. It is within the scope of the invention that the mini-hairpin primers have different loop sequences and/or different stem sequences. To be considered are the following: d(CGGAAAGC), d(GCGNAAGC) where N is either A (shown), G, C, or T. The 3' end is constituted by any combination of 3 or more nucleotides.

Further, RNA fragments like r(GCGAAAGC) also form a hairpin loop on the 5' end of a selected primer. It appears that preferably the arbitrary mini-hairpin oligonucleotide primers for use in the invention have 2 or more G-C base pairs as the stem region and contain 3 or 4 nucleotides in the loop region, including at least one A, preferred being either GAA or GA.

The arbitrary mini-hairpin oligonucleotide primers are very useful in conjunction with DAF, but also in any other multiple arbitrary amplicon profiling (MAAP) technique.

DNA amplification fingerprinting using arbitrary mini-hairpin oligonucleotide primers is carried out as follows. A modified primer was used to amplify arbitrary stretches of DNA from a DNA template using primers of related sequences as shown in FIG. 4, having at the 5' end a mini-hairpin (HP$_7$) of sequence GCGAAAGC. The method used was as follows: DAF reactions were done in a total volume of 20–25 μl containing 3 μM primer, 0.3 units/μl AmpliTaq Stoffel DNA polymerase (Perkin-Elmer/Cetus, Norwalk, Conn.), 200 μM of each deoxynucleoside triphosphates, 4 mM MgSO$_4$, 10 mM KCl, 4 mM (NH$_4$)$_2$SO$_4$, 0.1% Triton, 20 mM Tris-HCl (pH 8.3), and about 0.1 ng/μl of template DNA. The mixture was amplified in 35 cycles of 30 s at 96° C., 30 s at 30° C., and 30 s at 72° C. in a recirculating hot-air thermocycler (Bios, New Haven, Conn.). Amplification products were separated in polyester-backed 5% polyacrylamide-urea minigels and stained with silver as described in Caetano-Anolles et al. *Biotechnology* Vol. 9:553–557, (1991) incorporated herein by reference and attached (Exhibit 4). Wells were loaded with 3 μl of a ¹⁄₁₀ dilution of each amplification reaction mixed with 3 μl of loading buffer (5M urea and 0.02% xylene cyanol FF) and run at 100 V for about 80 min. Detection of DNA at the picogram level was by silver staining as described in Bassam et al. Anal. Biochem., Vol. 196, 80–83, (1991) as incorporated herein by reference and attached (Exhibit 5).

Using a mini-hairpin primer having only 3 nucleotides of arbitrary sequence gives a more reliable fingerprinting of small genomes as illustrated in Panels C and D of FIG. 4, respectively an *E. coli* strain and bacterial phage Lambda.

A close set of primers representing the 64 combinations of these 3' terminal nucleotides each having a 5' $HP_7$ is made available by following the procedure outlined above. Similar fingerprinting with bacterial phage Lambda is obtainable.

When it is desired to use more than 1 primer, 2 or more of the primers of the kit can be used.

In accordance with the invention, further new primers have been constructed in which one or more oligonucleotides at the 3' or the 5' terminus of the arbitrary primer have been substituted by a selected base. Illustrative bases are hypoxanthine (I), 6H,8H03,4-dihydropyrimido[4,5-c][1,2] oxazin-7-one (P) and 2-amino-6-methoxyaminopurine (K). Other bases may be considered. Likewise, any of the four bases, A, G,C, T can be replaced by another base. See FIG. 6 where 3 I represents inosine and N any one of the four bases: A, G, C, T.

From these studies, it appears that by the replacement of a nucleotide in such short primers, its discriminating function with respect to the priming site is at least in part hindered. The effective priming region has effectively become shorter and lost some of its specificity. This may have important applications not yet fully understood or explored.

In FIG. 6, it will be seen that fingerprints can also be tailored by having these substitutions. In some cases profiles simplify considerably (especially when I is introduced at the 3' end) in other the profiles become too complicated (by introducing degenerate bases at the 3' end).

The results presented herein above show that a primer for MAAP techniques need not contain more than 3 nucleotides at the 3' end which "screen" the target DNA possible sites and anneals to them and that the region which was hereinabove described as the "5' extension tail" is not essential when it is replaced in part or totally by an appropriate optimizer. An illustration provided by the invention is the hairpin primer. However, the concept of modifying the 5' domain of a primer is not limited to a hairpin modification. Any other modification which has an equivalent effect is contemplated to be within the scope of the invention. Chemical modification of the 5' end may be performed.

It is possible to fluorophore label the DNA 5' end of the primer with FAM, blue, JOE, green, TAMRA, yellow, or ROX, red. Efficient amplification takes place. An illustration is the primer GTGACGTAGG fluorescently labelled at its 5' end with FAM which was used to amplify two different turfgrass DNA samples. Amplification products can be separated using a Gene Scanner ABI 362. See, Applications of RAPD Technology to Plant Breeding, Joint Plant Breeding Symposia Series, Nov. 1, 1992, which is incorporated here by reference (Exhibit 6), and attached hereto. At least one primer may be biotinylated, i.e. covalently linked to biotin or an analog of biotin (biotin ovidin). Other groups designated as "reporter" groups can be used at the 5' end.

Another type of primer are those in which the 5' end is modified by a polyamide nucleic acid (PNA). Such polyamide is designed by replacing the deoxyribosephosphate backbone of DNA and with a achiralpolyamide backbone. Such oligomers recognize their complimentary target in double stranded DNA by strand displacement.

Accordingly, such primers comprise a 5' end of a DNA-PNA hybrid with a 3' end of 3 nucleotides (or more if desired), the DNA fragment constituting the balance of the primer such as 2 to 5 or 6 nucleotides, if desired. Typical PNA structures are shown in Nielsen et al., *Science, Vol.* 254:1497–1500 (1991) and Egholm et al. *Nature,,* Vol. 365:566–568 (1993) which are incorporated herein by reference and attached hereto (Exhibits 7 and 8).

The concept and implementation of a primer having a 5' end beyond the 7th, 8th or 9th nucleotide from the 3' end to optimize or increase the efficiency or functions of the 3' end is entirely novel, as far as could be determined. It is virtually impossible to describe all the means to accomplish this or an equivalent objective or result. It is not to be excluded that others skilled in the art might benefit from the teaching herein and apply it to their own purposes. Accordingly, it is contemplated by the inventors and it is their intention that substantially equivalent means performing in substantially in the same manner and accomplishing substantially the same or better result be considered within the scope of the invention though such may not fall within the literal wording of the claims.

As taught by the invention, the number of necessary oligonucleotides for fingerprint visualization has been determined to be 3. When a primer having an "optimizer" like a "hairpin" at its 5' end, it is not inconceivable however, that this number may be further reduced to its logical limit of one nucleotide. Moreover, one or more of the nucleotides of the 3 first nucleotides of the 3' end could be replaced by a degenerate base.

Further, it has been observed that the "hairpin" recognizes the template strands. It is therefore feasible to cause amplification without a core of nucleotides, thus using the hairpin as the primer.

The invention further provides means and methods for significantly further increasing the ability to detect polymorphisms. The method comprises digestion of a nucleic acid template with restriction endonucleases prior to amplification. This coupling of endonuclease cleavage and amplification of arbitrary stretches of DNA directed by short oligonucleotide primers allows ready distinction of closely related fungal and bacterial isolates, plant cultivars and eukaryotic organisms. MAAP analysis of cleaved template DNA identified molecular markers linked to a developmental locus of soybean (*Glycine max* L.). EMS-induced supernodulating near-isogenic lines altered in the nts locus that controls nodule formation could be distinguished from each other and from their parent cultivar by amplification of template pre-digested with 2–3 restriction enzymes. A total of 42 DNA polymorphisms were detected using only 19 octamer primers. In the absence of digestion, 25 primers failed to differentiate these soybean genotypes. Several polymorphic products co-segregated tightly with the nts locus in $F_2$ families from crosses between the allelic mutants nts382 and nts1007 and the ancestral *G. soja* Sieb. & Succ. PI468.397.

If desired, the pre-digestion may be followed by a post-digestion of the products of amplification with endonucleases.

Any primer may be used in this embodiment of the invention. The primers herein discussed may be particularly useful. Mixtures of primers are suitable. Amplification was carried out with pentamers, heptamers or octamers. Longer oligonucleotide primers can be used also. The predigestion is preferably carried out to completion.

In another aspect of the invention where restriction nuclease digest genomic DNA, the DNA can be of animal, plant or human sources, as in the other embodiments of the invention. The number of restriction fragments with which the primers will be made to react depends on the size of the genome and the frequency of occurrence of the target site of the restriction endonuclease in the genome, which in turn is primarily determined by the number of nucleotides in the target site. The number of nucleotides in the target sites of commonly used restriction endonucleases ranges from 4 to 8. The genome sizes of organisms vary widely from a few million base pairs in the case of microorganisms to several billion base pairs for animals and plants. Hence, the number of restriction fragments obtained after cleaving genomic DNA molecules with a restriction enzyme can vary from a few hundred to several million.

Any restriction endonuclease which recognizes a specific base sequence in a double stranded DNA and will cleave both strands of the DNA molecule at every target site can be used. Both blunt-end or staggered cutting endonucleases were used. The DNA sequence need not be a known sequence.

Typical useful endonucleases are the following: HaeIII, Sau3A, BamHI and MspI. Other restriction endonucleases are of course available and may be selected from Current Protocols in Molecular Biology, Vol. 1, ed. Ausubel et al., Section 3.1.6 through 3.1.20 which is incorporated herein by reference.

It is believed that cleavage at or near the restriction sites may make amplicons more readily available that are normally shielded and not available for replication.

For further description, see *Molecular General Genetics*, Vol. 241:64–67 (1993) incorporated herein by reference (Exhibit 9) and Applying DNA with Arbitrary Oligonucleotide Primers in *Review*, cited also and incorporated by reference and attached hereto.

DAF has been shown to be very useful to distinguish amongst closely related genotypes of prokaryotic and eukaryotiic organisms. There are situations were genetic improvements in certain plant strains and their respective contributions are particularly difficult to distinguish one from another and from the original strain.

The spectrum of nucleic acids characteristic of a particular nucleic acid genome generated in accordance with the invention, are useful per se not only for visualizing as described herein but also a starting nucleic acids fragments for further uses. Such pool or library of nucleic acid products can be obtained directly for the application of the process of the invention or by further treatment thereof, such by post-restriction endonuclease processing.

The application of the fingerprinting of the invention to mixed genomes is of great interest. Primers can be tailored to amplify preferentially and fingerprint a target genome in a mixture of their DNA fragments. An illustration of that situation is in nitrogen fixation. The Azolla-Anabaena symbiosis has been used for centuries as a nitrogen biofertilizer in rice paddies. Genetic improvement of the symbiosis has been limited by the difficulty in identifying Azolla-Anabaena accessions and Anabaena strains.

In this development, there were mixtures of DNA extracts from both prokaryotic Anabaena DNA and eukaryotic Azolla DNA. DAF could distinguish and positively identify accessions of Azolla-Anabaena with DNA extracted from intact symbiosis. For a detailed description see Plant Molecular Biology, Vol. 21:363–373 (1993) (Exhibit 10), which is incorporated herein by reference and attached hereto. Thus, there are circumstances in which it is helpful to use a complex mixture of nucleic acid, e.g. DNA fragments for amplification and profiling.

In accordance with the invention, multiple arbitrary primers can be used to generate fingerprints of prokaryotic and eukaryotic nucleic acids. Preferably the primers are of the same nucleotide length. Amplification products obtained using for instance two primers, produced a fingerprint which was not merely the result of adding amplification products obtained separately with each individual primer. Certain bands disappeared while other new ones were generated and few bands were shared. Each primer amplifies discrete and limited portions of a genome, producing a characteristic set of amplification products. Where a multiplicity of primers is used, new products arise from the overlap of the extension products initiated by each primer while others disappear. Alteratively, competition for annealing sites during amplification could result in a generation of new fingerprint patterns. The technique of using several primers has been nick-named "multiplex".

Furthermore, for some genomes which are difficult to separate, multiplex DAF is another approach for generating DNA fingerprints. Pooling of several primers can also increase the chances of finding polymorphic DNA. If there are difficulties to reveal polymorphisms between a set of cultivars, indication is that a subset of the primers in the mix could reveal these polymorphisms individually, so that multiplex DAF would provide an initial use for screening for closely relates species.

For RNA amplification using arbitrary primers (nick-named this procedure cDAF for complementary DNA amplification fingerprinting) clear fingerprints were also produced. In all cases the material was RNA extracted from roots of soybean cv. Bragg from the region of emergent root hairs. Primers used were CGCGGCCA, CGCGGCCA and TTTTTT (referred to as $T_6$), GCGC, GCGC and T6, CCTGT, CCTGT and $T_6$, AATGC, and finally AATGC and $T_6$. All combinations produced fingerprints. In the studies, 0.5 $\mu$g/$\mu$l RNA was reverse transcribed with 20 U MoMuLV reverse transcriptase in the presence of 1 $\mu$g total primers, 2 U RN Aasin and appropriate buffer containing nucleotides and magnesium chloride, by incubating the mixture at 23° C. for 10 min followed by an incubation at 42° C. for 30 min. The resulting reaction was treated as template for DAF analysis with the same primers used for transcription.

Multiple primers have been used in conjunction with various embodiments of the DAF invention. DNA amplification of turfgrass DNA using multiple primers was used to enhance understanding of genome divergents, cultivar identity and genetic mapping of relative adaptive gene loci. See Golf Course Management, Vol. 61:80–86 (1993) which is incorporated herein by reference and attached (Exhibit 11). Multiple primers used in these investigations were nucleotides GTATCGGC+GACGTAGG. A DNA polymerase used was the truncated derivative, the so-called Stoffel fragment of AmpliTaq (Perkin-Elmer/Cetus).

Fingerprinting of *Staphylococcus aureus* FDA 574 with mixtures of primers of sequences CGCGGCCA and GCTG-GTGG and of CGCGGCCA, GCTGGTGG and AATG-GAGC or revealed complex banding patterns. See *Biotechnology*, Vol. 9:553–557 (1991) cited above.

Other mixtures of primers ranging from 5 to 15 are useful in the practice of the invention. There may be used 2 or more primers. The resulting profiles of multiple primers are highly informative and may be preferred to the use of one primer in certain circumstances.

As known, most DNA polymerases perform primer extension reactions of the nucleic acid substrate consisting of a primer hybridizing to a template strand such that the 3' end of the primer is recessed relative to the 5' end of the template strand. The template strand is either a DNA or RNA. A DNA polymerase is used to extend the primer. For RNA templates, reverse transcriptase is an example of a nucleic acid polymerase that may be used. The choice of nucleic acid polymerase used in the extension reaction depends on the nature of the template.

It has been found in accordance with the invention that the truncated derivative, the so called Stoffel fragment of a DNA polymerase from *Thermos aquaticus* (AmpliTaq) is particularly useful. The Stoffel fragment is a highly thermostable, recombinant DNA polymerase, lacking the 289 N-terminal amino acids. It has a broad magnesium optimum, increased thermostability and no associated 3'–5' or 5'–3' exonuclease activity. The enzyme is described in a pamphlet from Perkins-Elmer/Cetus. The enzyme gave improved performance in DAF reactions and particularly is more efficient in amplification of short products and thus able to produce more informative fingerprints than other DNA polymerases. Preferably between about 0.2 and 0.4 units/μl of the Stoffel fragment produced clear and consistent results, whereas only 0.075 and 0.1 units/μl of AmpliTaq was suitable. Generally, the Stoffel fragment produced a broader distribution of amplification products each in greater amounts. This was especially evident with smaller products (less than 300 bp). Although both polymerases produced consistent fingerprints with 4 mM magnesium, the Stoffel enzyme was inhibited at a concentration higher than about 8 mM whereas the Stoffel fragment can tolerate concentration of magnesium up to about 12 mM.

Other DNA polymerase, preferably heat-stable which are at least substantially equivalent may be used like other N-terminally truncated *Thermus aquaticus* (Taq) DNA polymerase I. the polymerase named KlenTaq I and KlenTaq LA are quite suitable for that purpose. When KlenTaq I is substituted in the above described studies for the Stoffel fragment comparable results were obtained.

DNA from soybean cyst nematode (*Heterodera glycines*), and soybean DNA were amplified with primers GTAACGGCC and CCGAGCTG with KlenTaq I and KlenTaq LA.

In accordance with the invention, it has also been found that the annealing temperature in the cycling during the amplification reaction may be carried out within temperature ranges significantly above those commonly used heretofore, generally about 30° C.–35° C., the typical cycling parameters for PCR and RAPD.

It is noteworthy that primers of 7–15 nucleotides provided readable and meaningful profiles in the temperature range of about 15° C. through 75° C. The heptamers produced DNA amplification in the range of 15° C. through 60° C., preferably 45° C. through 60° C. A pentamer still produces DAF products at about 55° C. Octamers provide meaningful profiles in the range of about 15° to 65° C. It appears that DAF products are quite tolerant of annealing, extension, and denaturing times as opposed to other MAAP techniques.

Generally, amplification is carried through from 2 to as many cycles as is optimum to result in adequate number of amplified products for visualization such as up to 35 cycles, i.e. of 30 seconds at 96° C., 30 seconds at the appropriate annealing temperature and 30 seconds at 72° C. in a recirculating air-thermocycler (Bios, New Haven, Conn.).

Generally, especially for DAF products of less than about 500 bp, a two step cycling between the melting temperature (96° C.) and a non-stringent prime annealing temperature (in the ranges described) is sufficient for amplification.

An extension step is not necessary. Consistent products were obtained after 30–35 cycles and cycle numbers as high as 50 can be used without effecting fingerprint quality.

In accordance with the invention it has also been found that it is advantageous to use primer concentrations, than has been used heretofore, particularly relative to the amount of nucleic acid template. Whereas the prior art MAAP techniques other than DAF generally used DNA template concentration in excess of primer concentration, the DAF method provides concentration of primers in excess of DNA template.

to use about 3 μM primer concentrations for 7 mer to 15 mer primers, and about 10–30 μM concentrations for shorter primers (5 mer and 6 mer). For primers longer than 15 mer primer concentration less than 3 μM such as about 2 μM or less, gives satisfactory results. Amplification with pentamers are often performed with about 30 μM. Template concentrations generally used range from 0.1 ng/μl to 100 ng/pl. A minimum of 1 ng/μl template is sufficient to produce reliable fingerprints of low complexity genomes like prokaryotes or bacteriophage. A practical upper limit of template concentrations of 1 ng/μl appear quite satisfactory at this time.

A 3 μM solution of primer ranges from approximately 5 to 1 ng/μl for 5 mer to 10 mer primers, respectively.

With certain templates of high complexity eukaryotes (plants, animals, mammals, humans, etc.), there can be used as low as about 1 μg of total DNA (1 μg primer) defining a 1,000,000 ratio upper level. When using 0.2 μg total primer in the reaction, the upper level is preferably a 200,000 ratio primer/template.

Typically, to amplify bacteria with a 5 mer (5 ng/μl primer to 1 ng/μl template), the preferred ratio is about 5, which in some circumstances can be brought down to about 2. With an octamer( 8 ng/μl primer to 1 ng/μl template), the preferred ratio is about 8. To amplify complex genomes like soybean and mammals with a 5 mer (5 ng/μl primer to 0.1 ng/μl template) the ratio is about 50. For primers of 5 to 8 or 9 nucleotides, it is preferrred that the ratio be about 5 to 80 or 90, respectively. For an octamer, the ratio is about 80. A preferred practical range of minimum and maximum range of primer is preferably from about 2 to 1,000,000 relative to the template, preferably about 5 to about 200,000.

These parameters are provided as a guideline to one skilled in the art. It is contemplated that if one skilled in the art would work outside of these guidelines (ratios, limits, etc.), perhaps making other adjustments to other operative parameters, he would still be within the spirit if not the letter of the invention and its teaching.

In accordance with the invention it has been noted above that the various improvements in methodology and new products herein disclosed can be used individually in conjunction with what is called the DAF method or in general with MAAP methodologies, or in any combination thereof. For instance, the feature of the invention using an arbitrary mini-hairpin oligonucleotide primer for nucleic acid amplification fingerprinting with only 3 nucleotides can be applied to any existing MAAP techniques or others which will be hereinafter discovered. The mini-hairpin primers disclosed herein are expected to be useful in the amplification of any nucleic acid using polymerization with the described and other DNA or RNA polymerases. Equivalent primers having a 5' end which enhances the amplification of amplicons can also be used in other MAAP techniques. In accordance with the teaching of the invention reamplification of the products of the reaction can be performed whether or not such above-described primers were used. Likewise, the predigestion with endonuclease restriction enzymes can be applied to the heretofore DAF process alone or together with any of the other improvements disclosed herein. Likewise, the predigestion of the template by endonuclease restriction enzymes can be carried out on products traditionally used for other than DAF or MAAP processes, including the PCR methods.

See Mullis et al., U.S. Pat. No. 4,683,195 and Mullis et al., U.S. Pat. No. 4,683,202 which disclosed polymerase chain reactions which can be used to amplify any specific segment of nucleic acid.

Comparison of the products in accordance with the invention can be accomplished by a variety of techniques known to those skilled in the art. Inspection of the electrophoresis gel of the products reveals polymorphisms that affect the size and quantity of the amplified segment and polymorphisms that determine what segment is amplified. A preferred method for size fractionation is electrophoresis through a polyacrylamide gel or agarose gel matrix. A more preferred method of visualizing the products of the invention is by the method disclosed in the second parent patent application and in co-pending application Ser. No. 08/006,380. Other literature references that may be helpful in the visualization of the products of the invention are found in the various articles above referred to and which are hereby incorporated by reference.

Various text books and laboratory manuals which may be useful to one skilled in the art if desired include the following: Current Protocols, Vols. 1 and 2, ed. Ausubel et al.

As will be apparent to those skilled in the art, in light of the foregoing disclosure, many modifications, alternations and substitutions are possible in the practice of this invention without departing from the spirit or the scope thereof.

We claim:

1. A method for generating a profile characteristic of an unspecified nucleic acid sequence in a sample, which sequence is a template, which method comprises:
   a) treating the template with an oligonucleotide primer, wherein the primer has a double stranded stem of 2 complementary annealed base pairs, the double stranded stem extending to the 5' end of the primer and the other end of the stem extending as the single strand of at least 3 bases to the 3' end of the primer, and intermediate to the 5' and 3' ends of the stems a single stranded loop of 3 or 4 bases, the amount of primer being in excess over the amount of said nucleic acid, the amounts being in mass, and allowing said primer to anneal to multiple sites on each strand of said nucleic acid, each site being substantially complementary to the nucleotide of which said primer is constituted, thus, forming a multiplicity of a set of primed templates,
   b) treating said primed templates with a nucleic acid polymerase, thereby generating a multiplicity of extension strands, the extension strands comprising the primer in combination with a sequence of nucleotides that is substantially complementary to the templates, and extending along the template strands to either the 5' end of the template strands or the next primed site on the template, the number of extension strands thereby corresponding substantially to the number of primed sites,
   c) denaturing the extension strands from the template strands, thereby generating corresponding single-stranded extension strands and templates,
   d) allowing said primer to anneal to the extension strands and to the template strands,
   e) repeating steps (a), (b), (c) and (d), thereby generating nucleic acid fragments which are characteristic and unique for said nucleic acid of unspecified sequence, f) separating said fragments, and g) generating a characteristic profile of fragments from said sequence of nucleic acid in the sample.

2. The method of claim 1 wherein the ratio of the primer over the template is in the range of about 2 to about 1,000,000.

3. The method of claim 2 wherein the ratio of the primer over the template is in the range of about 5 to about 200,000.

4. The method of claim 1 wherein the loop has 3 bases.

5. The method of claim 1 wherein the loop has 4 bases.

6. The method of claim 1 wherein one of the bases of the loop is A.

7. The method of claim 1 wherein the length of the single strand is of 3 to 8 nucleotides.

8. The method of claim 1 wherein the primer is a deoxyribonucleotide sequence.

9. The method of claim 1 wherein the double stranded stem has two complementary GC pairs.

10. The method of claim 3 wherein the nucleotides of the loop are GAA.

11. The method of claim 5 wherein the nucleotides of the loop are GAAA or GTTA.

12. The method of claim 4 wherein the single strand comprises a sequence of nucleotides selected from the group consisting of CTG, GCTG, NCTG, GAGCTG, NAGCTG, and CCGAGCTG, wherein N is A, G, C, and T.

13. The method of claim 12 wherein N is G.

14. The method of claim 5 wherein the single strand has a sequence selected from the group consisting of GCTG and GAGCTG.

15. The method of claim 1 wherein the template is animal, human, mammal, plant, fungi or bacteria.

16. The method of claim 15 wherein the template is selected from the group consisting of soybean, Indonesian fruit bat, and *E. coli*.

17. The method of claim 1 wherein the sequence of the primer is known.

18. The method of claim 15 wherein the plant is turfgrass.

19. The method of claim 1 wherein the treatment of the template is performed with a mixture of two or more primers.

20. The method of claim 1 wherein the template is predigested with a restriction enzyme prior to step (a).

21. The method of claim 1 which comprises, after step (e) and before step (f), digesting generated fragments with a restriction endonuclease.

22. The separated fragments produced by the method of claim 1.

23. The method of claim 1 which comprises visualizing the characteristic pattern of said nucleic acid on a dried and developed polyacrylamide gel.

24. The developed and dried gel of claim 23 which is a permanent record of the characteristic pattern of said nucleic acid.

25. The method of claim 21 wherein the digested fragments are subjected to step (f) and (g).

26. The method of claim 19 wherein the primer mixture contains 5 to 15 primers.

27. The method of claim 1 wherein the sample comprises a mixture of nucleic acid sequences.

28. The method of claim 27 wherein the mixture comprises eukaryotic DNA and prokaryotic DNA.

29. The method of claim 1 wherein the first three bases of the 3' end are determinative to produce reproducible fingerprints.

30. The method of claim 1, which further comprises step (h), determining the characteristic profile of fragments generated from the sequence of nucleic acid in the sample.

31. A method for generating a profile characteristic of an unspecified nucleic acid sequence in A sample, which sequence is a template, which method comprises:

a) treating the template with an oligonucleotide primer of 5 to 25 nucleotides in length, the primer being of any nucleotide sequence and not of a particular sequence, the amount of primer being in excess over the amount of said nucleic acid, the amounts being in mass, and allowing said primer to anneal to multiple sites on each strand of said nucleic acid, each site being substantially complementary to the nucleotides of which said primer is constituted, thus forming a multiplicity of a set of primed templates, b) treating said primed templates with a nucleic acid polymerase, thereby generating a multiplicity of extension strands, the extension strands comprising the primer in combination with a sequence of nucleotides that is substantially complementary to the templates, and extending along the template strands to either the 5' end of the template strands or the next primed Site on the template, the number of extension strands thereby corresponding substantially to the number of primed sites, c) denaturing the extension strands from the template strands, thereby generating corresponding single-stranded extension strands and templates, d) allowing said primer to anneal to the extension strands and to the template strands, e) repeating steps (a), (b), (c) and (d), thereby generating nucleic acid fragments which are characteristic and unique for said nucleic acid of unspecified sequence, f) separating said fragments, and g) generating a characteristic profile of fragments from said sequence of nucleic acid in the sample.

32. The method of claim 31 wherein the primer is 7 to 15 nucleotides in length and the annealing temperature is between about 15 and 75° C.

33. The method of claim 32 wherein the primer is a heptamer and the annealing temperature is between 15 and 60° C.

34. The method of claim 31 wherein the ratio of the primer over the template is in the range of about 2 to about 1,000,000.

35. The method of claim 34 wherein the ratio of the primer over the template is in the range of about 5 to about 200,000.

36. The method of claim 35 wherein the primer has 5 to 8 nucleotides and the ratio of the primer over template is in the range of about 5 to about 80.

37. The method of claim 36 wherein the primer has 5 nucleotides, the template is a bacteria, and the ratio of the primer over template is about 5.

38. The method of claim 36 wherein the primer has 5 nucleotides, the template is a complex genome and the ratio is about 50.

39. The method of claim 36 wherein the primer has 8 nucleotides, the template is a bacteria, and the ratio of the primer over template is about 8.

40. The method of claim 36 wherein the primer has 8 nucleotides, the template is a complex genome and the ratio is about 80.

41. The method of claim 31 wherein the template is animal, human, mammal, plant, fungi or bacterial.

42. The method of claim 31 wherein the sequence of the primer is known.

43. The method of claim 41 wherein the plant is turfgrass.

44. The method of claim 31 wherein the template is an RNA template.

45. The method of claim 44 wherein the primer is selected from the group consisting of CGCGGCCA, TTTTTT, GCGC, GCGC and TTTTTT, CCTGT and TTTTTT, AATGC, and AATGC and TTTTTT.

46. The method of claim 31 wherein the template is predigested with a restriction enzyme prior to step (a).

47. The method of claim 31 which comprises, after step (e) and before step (f), digesting generated fragments with a restriction endonuclease.

48. The separated fragments produced by the method of claim 31.

49. The method of claim 31 which comprises visualizing the characteristic pattern of said nucleic acid on a dried and developed polyacrylamide gel.

50. The developed and dried gel of claim 49 which shows a permanent record of the characteristic pattern of said nucleic acid.

51. The method of claim 47 wherein the digested fragments are subjected to steps (f) and (g).

52. The method of claim 31 wherein one or more nucleotides at the 3' end or the 5' end of the primer is replaced by inosine (I) or N, wherein N is A, G, C, and T.

53. The method of claim 31 wherein the 5' end of the primer is labelled with a fluorophore radical.

54. The method of claim 32 wherein the primer is an octamer and the annealing temperature is between about 15 and 65° C.

55. The method of claim 31 wherein the first 5 bases at the 3' end define an essential core region.

56. The method of claim 31 wherein there is used more than one primer.

57. The method of claim 56 wherein the primers are of the same nucleotide length.

58. The method of claim 56 wherein multiple primers are CGCGGCCA and GCTGGTGG, or CGCGGCCA, GCTGGTGG and AATGGAGC.

59. The method of claim 56 wherein the primers are from 5 to 15 nucleotides in length.

60. The method of claim 31 wherein the nucleic acid sequence is an RNA sequence.

61. The method of claim 31 wherein the nuclei acid sequence is a DNA sequence.

62. The method of claim 31 wherein the primer has a 3' and a 5' end and the 5' end is modified.

63. The method of claim 62 wherein the modification is a chemical modification.

64. The method of claim 63 wherein the 5' end has a fluorophore label, or a polyamide nucleic acid.

65. The process of claim 31 wherein the primer has a 3' and a 5' end in which one or more of the four A,G,C, and T bases is replaced by another base.

66. The process of claim 65 wherein the other base is selected from the group consisting of hypoxanthine 6H, 8H03, 4-dihydropyrimido[4,5-c][1,2]oxazin-7-one and 2-amino-6-methoxyaminopurine.

67. The method of claim 31, which further comprises step (h), determining the characteristic profile of fragments generated from the sequence of nucleic acid in the sample.

68. The method of claim 31 wherein the sequence of the primer is known.

69. The method of claim 31 which is performed on a multiplicity of nucleic acid samples and which further comprises comparing the profiles obtained from the samples.

70. The method of claim 69 wherein the samples are DNA samples.

71. A method for generating a profile characteristic of an unspecified nucleic acid sequence in a sample, which sequence is a template, which method comprises:

a) treating the template with a first oligonucleotide primer of 5 to 25 nucleotides in length, the primer being free of secondary structure, the amount of primer being in excess over the amount of said nucleic acid, the amounts being in mass, and allowing said primer to anneal to multiple sites on each strand of said nucleic acid, each site being substantially complementary to the nucleotides of which said primer is constituted, thus forming a multiplicity of a set of primed templates, b) treating said primed templates with a nucleic acid polymerase, thereby generating a multiplicity of extension strands, the extension strands comprising the primer in combination with a sequence of nucleotides that is substantially complementary to the templates, and extending along the template strands to either the 5' end of the template strands or the next primed site on the template, the number of extension strands thereby corresponding substantially to the number of primed sites, c) denaturing the extension strands from the template strands, thereby generating corresponding single-stranded extension strands and templates, d) allowing said primer to anneal to the exterior strands and to the template strands, e) repeating steps (a), (b), (c) and (d) until there are generated nucleic acid fragments which are characteristic and unique for said nucleic acid of unspecified sequence, f) repeating steps (a), (b), (c), (d), and (e) on said fragments with a second oligonucleotide primer of 5 to 25 nucleotides in length, thereby generating a second set of fragments, g) separating said second set of fragments, and h) generating a characteristic profile of fragments from said sequence of nucleic acid in the sample.

72. The method of claim 71 wherein the first and second primers are of different lengths.

73. The method of claim 72 wherein the first and second primers have a common sequence.

74. The method of claim 73 wherein the second primer is longer than the first primer.

75. The method of claim 73 wherein the second primer is shorter than the first primer.

76. The method of claim 71 wherein the first and second primers have the same sequence and number of nucleotides.

77. The method of claim 71 wherein the sequence of the primer is known.

78. The method of claim 71 wherein the template is all RNA template.

79. The separated second set of fragments produced by the method of claim 71.

80. The method of claim 71 which comprises visualizing the characteristic pattern of said nucleic acid on a dried polyacrylamide gel on which the pattern is developed.

81. The developed and dried gel of claim 80 which contains and shows a permanent record of the characteristic pattern of said nucleic acid.

82. The method of claim 71 wherein the first primer is of any nucleotide sequence.

83. The method of claim 71, which further comprises step (i), determining the characteristic profile of fragments generated from the sequence of nucleic acid in the sample.

* * * * *